(12) United States Patent
Martinez Climent et al.

(10) Patent No.: US 11,672,463 B2
(45) Date of Patent: Jun. 13, 2023

(54) DEVICE FOR IDENTIFYING THE SITE OF CARDIAC ARRHYTHMIAS

(71) Applicants: Fundación Para La Investigación Biomedica Del Hospital Gregorio Maranon, Madrid (ES); Universität Politécnica De Valencia, Valencia (ES)

(72) Inventors: Andreu Martinez Climent, Madrid (ES); Felipe Atienza Fernandez, Madrid (ES); Angel Arenal, Madrid (ES); Francisco Fernandez Aviles, Madrid (ES); Maria S. Guillem Sanchez, Madrid (ES)

(73) Assignees: FUNDACION PARA LA INVESTIGACION BIOMEDICA DEL HOSPITAL GREGORIO MARANON, Madrid (ES); UNIVERSITAT POLITECNICA DE VALENCIA, Valencia (ES)

( * ) Notice: Subject to any disclaimer, the term of this patent is extended or adjusted under 35 U.S.C. 154(b) by 396 days.

(21) Appl. No.: 15/522,590

(22) PCT Filed: Oct. 29, 2015

(86) PCT No.: PCT/ES2015/070779
§ 371 (c)(1),
(2) Date: Nov. 9, 2017

(87) PCT Pub. No.: WO2016/066879
PCT Pub. Date: May 6, 2016

(65) Prior Publication Data
US 2018/0132741 A1    May 17, 2018

(30) Foreign Application Priority Data

Oct. 30, 2014   (ES) ................. ES201431597

(51) Int. Cl.
*A61B 5/361*   (2021.01)
*G06T 17/00*   (2006.01)
(Continued)

(52) U.S. Cl.
CPC ............ *A61B 5/361* (2021.01); *A61B 5/0035* (2013.01); *A61B 5/24* (2021.01); *A61B 5/25* (2021.01);
(Continued)

(58) Field of Classification Search
CPC ..... A61B 5/046; A61B 5/0417; A61B 5/0408; A61B 5/0044; A61B 18/1492; A61B 2576/023; G16H 50/50
(Continued)

(56) References Cited

U.S. PATENT DOCUMENTS 5,687,737 A * 11/1997 Branham ............... A61B 5/287
600/509
6,545,678 B1 * 4/2003 Ohazama ............... G06T 17/00
382/128
(Continued)

FOREIGN PATENT DOCUMENTS

GB     2503055 A   12/2013
WO     9905962 A1   2/1999
(Continued)

OTHER PUBLICATIONS

Konings et al.; "High-Density Mapping of Electrically Induced Atrial Fibrillation in Humans"; Circulation; Apr. 1994 pp. 1665-1680; vol. 89 No. 4; American Heart Association, Inc.; Dallas.
(Continued)

*Primary Examiner* — Carl H Layno
*Assistant Examiner* — Michael J Lau
(74) *Attorney, Agent, or Firm* — Hayes Soloway PC

(57) ABSTRACT

The device for locating cardiac arrhythmias comprises a three-dimensional reconstruction of the patient's torso and a
(Continued)

number of surface electrodes, wherein the three-dimensional reconstruction of the patient's torso is generated through a number of images obtained by means of at least one camera. In particular, the device comprises elements for locating the surface electrodes, which detect the position of the electrodes with respect to the patient's torso, and data processing elements that generate, on the basis of the three-dimensional reconstruction and the position of the electrodes, a surface electrocardiographic map, and said surface electrocardiographic map has a number of data corresponding to readings of the surface electrodes related to areas of the three-dimensional reconstruction.

10 Claims, 1 Drawing Sheet

(51) Int. Cl.
    *A61B 5/00*         (2006.01)
    *A61B 5/24*         (2021.01)
    *A61B 5/25*         (2021.01)
    *A61B 5/282*       (2021.01)
    *A61B 5/316*       (2021.01)
    *A61B 5/318*       (2021.01)
    *G16H 50/50*      (2018.01)
    *A61B 5/287*       (2021.01)
    *A61B 18/14*       (2006.01)

(52) U.S. Cl.
    CPC .............. *A61B 5/282* (2021.01); *A61B 5/316* (2021.01); *A61B 5/318* (2021.01); *A61B 5/7278* (2013.01); *G06T 17/00* (2013.01); *G16H 50/50* (2018.01); *A61B 5/0044* (2013.01); *A61B 5/287* (2021.01); *A61B 18/1492* (2013.01); *A61B 2576/023* (2013.01)

(58) Field of Classification Search
    USPC ......................................................... 600/515
    See application file for complete search history.

(56) References Cited

U.S. PATENT DOCUMENTS

| | | | | |
|---|---|---|---|---|
| 6,584,343 B1* | 6/2003 | Ransbury | ............. | A61B 5/6841 600/509 |
| 7,433,730 B1* | 10/2008 | Berrier | ................... | A61B 5/287 600/509 |
| 7,729,752 B2* | 6/2010 | Harlev | ................. | A61B 5/4848 600/509 |
| 7,805,179 B2* | 9/2010 | Horng | ................... | A61B 5/243 600/409 |
| 8,478,393 B2* | 7/2013 | Ramanathan | .......... | A61B 5/316 600/509 |
| 8,725,241 B2* | 5/2014 | Ramanathan | .......... | G16H 40/63 600/525 |
| 2002/0128565 A1* | 9/2002 | Rudy | .................... | A61B 5/6856 600/509 |
| 2003/0018277 A1* | 1/2003 | He | ......................... | A61B 5/318 600/544 |
| 2003/0158477 A1* | 8/2003 | Panescu | ................. | A61B 34/20 600/424 |
| 2004/0006265 A1* | 1/2004 | Alhussiny | .............. | A61B 5/318 600/509 |
| 2004/0082870 A1* | 4/2004 | Rudy | .................... | A61B 5/6855 600/509 |
| 2005/0043604 A1* | 2/2005 | Beatty | .................. | A61B 5/1076 600/374 |
| 2005/0228626 A1* | 10/2005 | Simelius | ................ | G16H 50/20 703/11 |
| 2007/0106146 A1* | 5/2007 | Altmann | .............. | A61B 6/5247 600/407 |
| 2007/0270703 A1* | 11/2007 | He | ......................... | A61B 5/287 600/509 |
| 2008/0058657 A1* | 3/2008 | Schwartz | ............. | A61B 5/6805 600/508 |
| 2008/0177192 A1* | 7/2008 | Chen | ...................... | A61B 6/503 600/509 |
| 2008/0177280 A1* | 7/2008 | Adler | ...................... | A61B 90/10 901/41 |
| 2009/0099563 A1* | 4/2009 | Ciaccio | ................... | A61B 90/36 606/41 |
| 2009/0264781 A1* | 10/2009 | Scharf | .................... | A61B 5/282 600/509 |
| 2010/0106009 A1* | 4/2010 | Harlev | ................... | A61B 5/065 600/424 |
| 2010/0198101 A1* | 8/2010 | Song | ..................... | A61B 5/0871 600/547 |
| 2010/0249623 A1* | 9/2010 | Makdissi | ............. | A61N 1/3925 600/509 |
| 2011/0034912 A1* | 2/2011 | de Graff | ........... | H01L 27/14632 606/41 |
| 2011/0069159 A1* | 3/2011 | Soler | ...................... | A61B 90/36 348/E7.085 |
| 2011/0080471 A1* | 4/2011 | Song | ..................... | G06T 7/521 356/627 |
| 2011/0190649 A1* | 8/2011 | Rudy | ..................... | A61B 5/316 600/509 |
| 2011/0275921 A1* | 11/2011 | Revishvili | .............. | A61B 5/055 600/382 |
| 2012/0035459 A1* | 2/2012 | Revishvili | .............. | A61B 5/318 600/411 |
| 2012/0157822 A1* | 6/2012 | van Dam | ................ | A61B 5/318 600/513 |
| 2012/0215094 A1* | 8/2012 | Rahimian | ............. | A61B 6/504 600/414 |
| 2012/0219195 A1* | 8/2012 | Wu | ........................ | A61B 5/243 382/128 |
| 2012/0271162 A1* | 10/2012 | Liao | ........................ | G06T 7/285 600/424 |
| 2012/0283587 A1* | 11/2012 | Gosh | ........................ | A61B 5/02 600/510 |
| 2013/0060315 A1* | 3/2013 | Elghazzawi | ......... | A61N 1/3993 607/142 |
| 2013/0096394 A1* | 4/2013 | Gupta | ................... | A61B 5/4848 600/301 |
| 2013/0131531 A1* | 5/2013 | Olson | ..................... | A61B 5/743 600/523 |
| 2013/0184697 A1* | 7/2013 | Han | ....................... | A61B 90/37 606/32 |
| 2013/0245473 A1* | 9/2013 | Ramanathan | ........ | A61B 5/0044 600/509 |
| 2013/0304407 A1* | 11/2013 | George | ................ | A61B 5/7203 702/72 |
| 2013/0317337 A1* | 11/2013 | Wu | ........................ | A61B 5/243 600/409 |
| 2014/0031668 A1* | 1/2014 | Mobasser | ............... | A61B 5/055 600/417 |
| 2014/0142435 A1* | 5/2014 | Bernal | ................. | A61B 5/1135 600/476 |
| 2014/0163368 A1* | 6/2014 | Rousso | ................ | A61B 6/4258 600/436 |
| 2014/0193336 A1* | 7/2014 | Rousso | ................... | A61B 6/503 600/431 |
| 2014/0200823 A1* | 7/2014 | Zeng | ...................... | A61B 5/30 702/19 |
| 2014/0200874 A1* | 7/2014 | Zeng | ..................... | A61B 5/339 703/11 |
| 2014/0205165 A1* | 7/2014 | Jeanne | .................. | G16H 30/00 382/128 |
| 2014/0278129 A1* | 9/2014 | Voth | ........................ | A61B 5/287 702/19 |
| 2014/0303452 A1* | 10/2014 | Ghaffari | ................ | A61B 18/14 601/3 |

(56) References Cited

U.S. PATENT DOCUMENTS

FOREIGN PATENT DOCUMENTS

| WO | 2012110940 A1 | 8/2012 |
| WO | 2013006724 A2 | 1/2013 |
| WO | 2013056050 A1 | 4/2013 |
| WO | 2014118535 A2 | 8/2014 |

OTHER PUBLICATIONS

Mansour Md et al.; "Left-to-Right Gradient of Atrial Frequencies During Acute Atrial Fibrillation in the Isolated Sheep Heart"; Circulation; May 29, 2001; pp. 2631-2636; vol. 103; American Heart Association, Inc.; Dallas.

Jalife et al.; "Mother rotors and fibrillatory conduction: a mechanism of atrial fibrillation"; Cardiovascular Research 2002; pp. 204-216; vol. 54; Elsevier Science B.V.

Yesim Serinagaoglu, "Improved Performance of Bayesian Solutions for Inverse Electrocardiography Using Multiple Information Sources", Journal, 2006, 2024-2034, vol. 53, No. 10, IEEE Transactions on Biomedical Engineering.

* cited by examiner

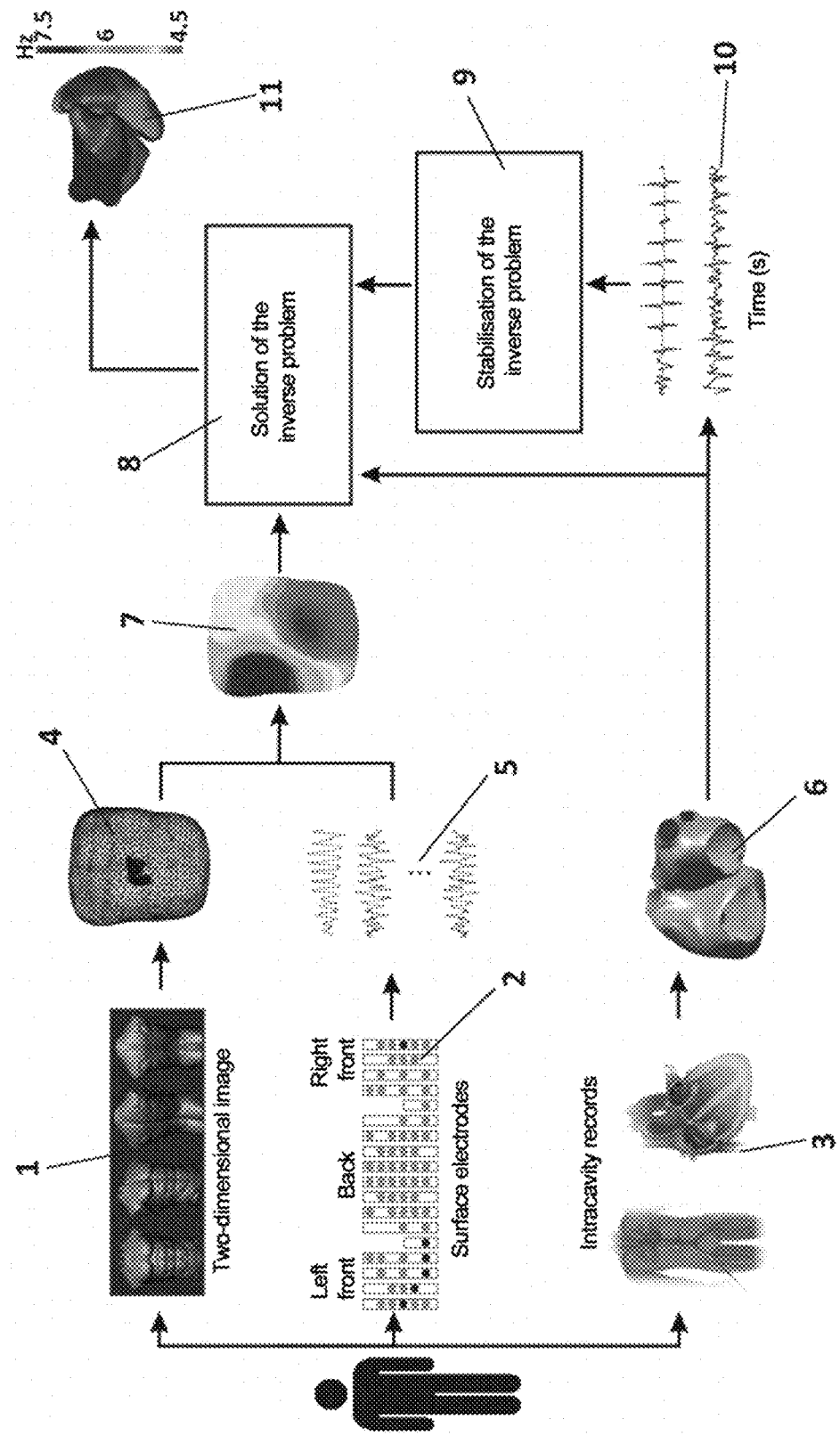

DEVICE FOR IDENTIFYING THE SITE OF CARDIAC ARRHYTHMIAS

OBJECT OF THE INVENTION

The present invention discloses a device for locating cardiac arrhythmias and, in particular, for locating and detecting the cardiac regions responsible for arrhythmias with patterns that are not necessarily stochastic, such as, for example, atrial fibrillation.

BACKGROUND OF THE INVENTION

Cardiac arrhythmias are the main cause of death in Europe. Currently, treatment of said arrhythmias by means of ablation is performed by the electrical isolation of the cardiac region that causes the onset and/or maintenance of each arrhythmia. For this reason, the key to adequately treating said arrhythmias lie in the detection of the target cardiac region for the ablation process. Currently, said detection is performed by means of catheterisation processes, which invasively and sequentially map cardiac activity and, if the arrhythmia has a stable pattern, locate the target ablation region.

Although this process is effective in the case of arrhythmias with stable patterns, said process has significant limitations for arrhythmias with non-stationary activation, such as, for example, atrial fibrillation.

On the other hand, there exist non-invasive electrocardiographic mapping systems for the simultaneous reconstruction of cardiac activity in the cardiac chambers. One example of said systems is disclosed in document WO2013006724A2 (Cardioinsight). Despite the advantages offered by these systems, the solutions presented thus far have significant limitations.

In the first place, correct operation of the equipment requires constructing a model of the patient's torso on the basis of computerised axial tomography or magnetic resonance images prior to the process, which increases the cost thereof and hinders its clinical implantation. Moreover, the equipment used in said processes is significantly limited in its capacity to precisely reconstruct cardiac activity on the basis of the signals recorded on the torso during irregular arrhythmias with multiple wavefronts such as, for example, atrial fibrillation. Specifically, the epicardial potential maps reconstructed by means of quadratic stabilisation functions show a paradoxically simple electrical activity that is in contrast with the complexity observed in both invasively recorded electrograms [Konings KTS, et al. High-density mapping of electrically-induced atrial fibrillation in humans. Circulation 1994; 89:1665-1680] and optical mapping records during atrial fibrillation in animal models [Mansour M, et al. Left-to-right gradient of atrial frequencies during acute atrial fibrillation in the isolated sheep heart. Circulation 2001; 103:2631-2636, and Jalife J, et al. Mother rotors and fibrillatory conduction: a mechanism of atrial fibrillation. Cardiovasc Res 2002; 54:204-216.]. The different behaviour of traditional techniques for solving the inverse problem when addressing organised and disorganised electrical activities may be explained on the basis of the mathematical formulation of the inverse problem of electrocardiography, which is usually posed as an optimisation problem, and wherein a compromise is sought between the similarity between the potentials recorded on the torso and the potentials that the estimated epicardial potentials would generate on the torso, and the homogeneity in the estimated epicardial potentials. Although minimising the homogeneity in epicardial potentials makes it possible to obtain robust solutions against noise, it involves excessive simplification in the estimated potentials during irregular arrhythmias, such as, for example, atrial fibrillation.

DESCRIPTION OF THE INVENTION

The present invention discloses a device that solves the problems in the prior art, insofar as it incorporates more real-time information, which makes it possible to more accurately locate the cardiac region responsible for the onset and/or maintenance of irregular cardiac arrhythmias. In fact, the present invention makes it possible to characterise cardiac electrophysiological behaviour by means of the combined analysis of the overall information obtained by means of mapping and, optionally, intracavity information obtained by means of catheters. Consequently, the method applied may be implemented non-invasively or, alternatively, with less invasion of the patient than with already-known methods and devices, which would contribute to increasing the accuracy of the data obtained.

In particular, the present invention discloses a device for locating cardiac arrhythmias that comprises a three-dimensional reconstruction of a patient's torso and a number of surface electrodes, which comprises:
  three-dimensional reconstruction elements that generate the three-dimensional reconstruction of the patient's torso through a number of images obtained by means of at least one camera;
  elements for locating the surface electrodes, which detect the position of the electrodes with respect to the patient's torso;
  data processing elements that generate, through the three-dimensional reconstruction and the position of the electrodes, a surface electrocardiographic map.
said surface electrocardiographic map comprising a number of data corresponding to readings of the electrodes related to areas of the three-dimensional reconstruction.

Preferably, the elements for locating the surface electrodes detect the position of the electrodes by processing the images obtained using at least one camera.

In regards to the cameras, the present invention considers, as an example, that said cameras may visible imaging cameras and/or angiographic cameras. Moreover, it considers that, for the three-dimensional reconstruction of the patient's torso, at least two images are required, which may be obtained by one camera taking images from different positions or by a number of cameras located at different sites.

In particular, the surface electrocardiographic map comprises elements for detecting the area of the torso that presents a cardiac arrhythmia. This is performed by processing the signals originating from the surface electrodes and correlating these signals with the areas of the body where each of the electrodes is placed. In this way, it is possible to determine to which electrode a signal of arrhythmia corresponds and, consequently, the area where it is located.

In an especially preferred embodiment, the present invention uses at least one intracavity catheter. The use of this intracavity catheter provides a greater amount of data to the device, which allows for higher precision in regards to the area that presents the arrhythmia.

If, in addition to having at least one intracavity catheter, there are elements for locating intracavity catheters, it is possible to generate, using elements for generating anatomical reconstructions, an intracavity anatomical reconstruction, i.e. a three-dimensional representation with the dimensions of the heart and each of its cavities, as well as the electrical signals corresponding to each of said cavities (signals originating from the external electrodes as well as from the intracavity electrodes). This is obtained by solving what, hereinafter, will be called the inverse problem, which is solved by combining quadratic and non-quadratic stabilisation functions under discontinuity conditions.

Moreover, the present invention considers that the processing elements, using the intracavity anatomical reconstruction and the surface electrocardiographic map, may generate an electroanatomical map wherein the electrical activity of each area is identified and, furthermore, that, on the basis of said electroanatomical map, elements for detecting cardiac arrhythmias may be obtained.

DESCRIPTION OF THE DRAWINGS

In order to supplement the description being made, and to contribute to a better understanding of the characteristics of the invention, according to a preferred embodiment thereof, a set of drawings is attached to said description as an integral part thereof, where the following is represented for illustrative, non-limiting purposes:

FIG. 1.—Shows a schematic view of the device for detecting cardiac arrhythmias according to the present invention, as well as the detection method.

PREFERRED EMBODIMENT OF THE INVENTION

FIG. 1 shows a preferred embodiment of the present invention. In this embodiment, it may be observed that the device essentially involves taking three measurements.

The first measurement involves performing a three-dimensional reconstruction (4) of the patient's torso by means of a set of images (1), for example, two-dimensional images obtained by means of a camera. This reconstruction is performed by means of at least two photographs taken using image processing techniques that are widely known in the prior art.

The second measurement is a surface electrocardiographic map. This map is performed by taking data from a number of surface electrodes (2) and associating the data taken from said electrodes with a particular area of the patient's body. The data obtained by means of said electrodes are a number of electrical signals (5) obtained non-invasively (without any surgical procedure whatsoever). Moreover, as mentioned above, it is important to find a correlation between the electrical signals (5) and the position of the electrode that has taken each of the signals, in order to determine to which part of the heart each signal corresponds.

Consequently, the present invention considers elements for detecting the position of the electrodes. This detection of the position of the electrodes is most preferably performed by means of image analysis, in particular, analysis of the images (1) with which the three-dimensional reconstruction (4) of the patient's torso is performed, or, alternatively, of other images obtained using the same elements for obtaining images. On the basis of this detection, a correlation between the electrical data and the position of the electrodes with respect to the patient's body may be performed, i.e. we may obtain a three-dimensional reconstruction (4) of the patient's torso, the position of the electrodes on the torso and the electrical signals measured for each of the points of the torso, and, with these data, obtain a surface electrical map that is nothing less than the combination of all these data into a graphic representation.

Although on the basis of these data we could already have a three-dimensional representation of the functioning of each of the areas of the heart and locate cardiac arrhythmias, the present invention considers that, in order to increase the accuracy in locating the area wherein said arrhythmias appear, intracavity records may be taken (3) by using at least one catheter. Although this process is intrusive, it requires less intrusion than the mapping processes in the prior art.

Basically, for this measurement, there is a catheter inside the heart that sequentially measures the activity at various points in the atrium. The position of this catheter at each moment may be determined using elements for detecting the position of the catheter (for example, using two-dimensional photographs of the type used to perform the three-dimensional reconstruction (4)). Once the activity has been measured at several points and recorded in several intracavity records (3), we may obtain an intracavity anatomical reconstruction (6), which may be used for the reconstruction of the epicardium (i.e. an intracavity anatomical reconstruction) on the basis of the non-invasive records, using a regularisation of the solution of the inverse problem (8) based on quadratic and non-quadratic stabilisation functions under spatio-temporal discontinuity conditions. In this way, the signals calculated on the basis of the non-invasive records are used for the representation of the epicardial electroanatomical maps (11).

It is worth mentioning that the intracavity mapping (3) is not essential for the system to calculate the epicardial potentials, which are calculated on the basis of the non-invasive surface records by solving the inverse problem, but using a few intracavity points is very helpful for a reliable reconstruction of the mathematical problem, which guarantees reliability even during irregular arrhythmias, such as atrial fibrillation.

Once the activity has been measured at several intracavity points (3), we may obtain an intracavity anatomical reconstruction (6), which may be used for the reconstruction of the epicardium on the basis of the non-invasive records, by using a regularisation of the solution of the inverse problem based on quadratic and non-quadratic stabilisation functions under spatio-temporal discontinuity conditions, i.e. an electroanatomical correlation (8) is made taking into consideration the data obtained by means of the surface electrocardiographic map (7) and the intracavity anatomical reconstruction (6).

Specifically, the solution of the inverse problem is performed by means of the iterative estimation of the transfer matrix between the potentials in the atrial epicardium ($U_A$) and the potentials on the torso ($U_T$):

$$MU_A = U_T$$

This is an ill-conditioned problem, since the number of estimated points on the surface of the epicardium (e.g. 2000 epicardial points) is much larger than the number of potentials on the torso (e.g. 120 electrodes on the torso). For this reason, calculation of the inverse transfer matrix is performed by minimising the error according to the following equation:

$$\min\{|MU_A(\lambda) - U_T|^2 + \lambda \|BU_A(\lambda)\|^2\}$$

where $\lambda$ is a regularisation parameter and B is the spatial regularisation matrix. Calculation of the optimal transfer matrix M is performed by means of the iterative solution of the problem for various temporal and spatial regularisation values, in order to ensure an appropriate representation of the power distribution within the frequency spectrum.

In addition to what has been discussed above, the intracavity electrical signals (10) obtained by means of the intracavity catheter may be taken as an anchor and validation point for the reconstruction of the entire epicardial map on the basis of the non-invasive signals, in order to perform a stabilisation (9) of the inverse problem through the spatio-temporal correlation of the intracavity recording points according to the time, phase, modulus, spectrum and causality information. This makes it possible to reconstruct the activity of the entire atrium in a quick, reliable manner, even during irregular arrhythmias, such as atrial fibrillation.

What is claimed is:

1. A device for locating and detecting the cardiac regions responsible for irregular cardiac arrhythmias, the device comprising:
    a three-dimensional reconstruction element that generates a three-dimensional reconstruction of a surface of a patient's torso through processing a plurality of images, including a number of images of the surface of the patient's torso obtained by at least one camera, wherein at least one camera is a visible imaging camera, wherein the number of images is at least two and wherein images are taken from different positions;
    image analysis element for locating a plurality of surface electrodes, wherein the plurality of surface electrodes are positioned on the patient's torso and whereby the image analysis element detects the position of the electrodes with respect to the surface of the patient's torso, wherein the image analysis element detects the position of the electrodes by processing the images with which the three-dimensional reconstruction of the patient's torso is performed;
    data processing elements that correlate a number of readings of the surface electrodes to the three-dimensional reconstruction and the position of the surface electrodes to generate a surface electrocardiographic map, and
    a display for receiving and displaying the surface electrocardiographic map.

2. The device of claim 1, further comprising an angiographic camera.

3. The device of claim 1, wherein the device comprises processing elements for locating the area of the torso that presents a cardiac arrhythmia.

4. The device of claim 1, comprising at least one intracavity catheter having at least one electrode that takes intracavity readings.

5. The device of claim 4, comprising elements for locating intracavity catheters.

6. The device of claim 5, comprising elements for generating an intracavity anatomical reconstruction on the basis of the intracavity readings and the elements for locating the intracavity catheters.

7. The device of claim 6, wherein, by correlating the data from the intracavity anatomical reconstruction and the surface electrocardiographic map, the processing elements generate an electroanatomical map wherein the electrical activity of each area is identified.

8. The device of claim 7, comprising elements for detecting cardiac arrhythmias in the electroanatomical map.

9. The device of claim 6 further comprising a processor receiving information from the intracavity readings and the surface electrocardiographic map and performing an iterative estimation of a transfer matrix between a plurality of atrial epicardium potentials ($U_A$) and torso potentials ($U_T$) using an equation: $MU_A=U_T$.

10. The device of claim 9, wherein performing the iterative estimation further comprises solving the following equation:

$$\min\{|MU_A(\lambda)-U_T|^2+\lambda\|BU_A(\lambda)\|^2\}$$

Where $\lambda$ is a regularization parameter and B is a spatial regularization matrix.

* * * * *